US006162430A

United States Patent [19]
Hammock et al.

[11] Patent Number: 6,162,430

[45] **Date of Patent: *Dec. 19, 2000**

[54] INSECT CONTROL WITH MULTIPLE TOXINS

[75] Inventors: Bruce D. Hammock, Davis, Calif.; Rafael Herrmann, Kiryat Bialic; Haim Moskowitz, Jerusalem, both of Israel

[73] Assignee: The Regents of the University of California, Oakland, Calif.

[ * ] Notice: This patent is subject to a terminal disclaimer.

[21] Appl. No.: 09/020,216

[22] Filed: Feb. 6, 1998

Related U.S. Application Data

[62] Division of application No. 08/435,040, May 8, 1995, Pat. No. 5,756,340.

[51] Int. Cl.[7] .......................... A01N 63/00; A01N 37/18; C07K 14/435; C07K 2/00

[52] U.S. Cl. ............................... 424/93.2; 514/12; 514/2; 530/300; 530/324; 530/858

[58] Field of Search ......................... 514/12, 2; 424/93.2; 530/300, 324, 858

[56] References Cited

U.S. PATENT DOCUMENTS

| | | | |
|---|---|---|---|
| 4,668,511 | 5/1987 | Aspirot et al. | 424/93.6 |
| 4,745,051 | 5/1988 | Smith et al. | 435/69.51 |
| 4,762,547 | 8/1988 | Iwasaki et al. | 504/330 |
| 4,870,023 | 9/1989 | Fraser et al. | 435/235.1 |
| 4,888,340 | 12/1989 | Neh et al. | 514/403 |
| 4,929,718 | 5/1990 | Possani et al. | 530/326 |
| 5,071,748 | 12/1991 | Miller | 435/69.1 |
| 5,098,706 | 3/1992 | Hammock et al. | 424/93.2 |
| 5,162,308 | 11/1992 | Brown et al. | 514/63 |
| 5,177,308 | 1/1993 | Barton et al. | 800/302 |
| 5,180,581 | 1/1993 | Miller et al. | 424/93.2 |
| 5,238,724 | 8/1993 | Bjostad, III et al. | 424/84 |
| 5,266,314 | 11/1993 | Maeda | 424/93.2 |
| 5,266,317 | 11/1993 | Tomalski et al. | 424/93.2 |
| 5,457,178 | 10/1995 | Jackson et al. | 530/350 |
| 5,770,192 | 6/1998 | Cayle et al. | 424/93.2 |

FOREIGN PATENT DOCUMENTS

| | | |
|---|---|---|
| 0222412B | 11/1986 | European Pat. Off. . |
| 0225777 | 12/1986 | European Pat. Off. . |
| 374753A2 | 6/1990 | European Pat. Off. . |
| 374753A3 | 6/1990 | European Pat. Off. . |
| 431829A1 | 6/1991 | European Pat. Off. . |
| 477676A1 | 4/1992 | European Pat. Off. . |
| 505207A1 | 9/1992 | European Pat. Off. . |
| 2074868 | 3/1981 | United Kingdom . |
| 94/03588 | 2/1994 | WIPO . |

OTHER PUBLICATIONS

Kopeyan et al. Primary structure of toxin IV of Leiurus quinquestriatus quinquestriatus. Characterization of a new group of scorpion toxins. FEBS Lett. 181(2), 211–17, 1985.
Hammock et al., "The Role of Juvenile Hormone Metabolism in the Metamorphosis of Selected Lepidoptera," *Chemical Abstracts*, 102 (1985), entry 76006b.

Abdel–Aal and Hammock, "3–Octylthio–1,1,1–trifluoro–2–propanone, A High Affinity and Slow Binding Inhibitor of Juvenile Hormone Esterase from *Trichoplusia ni* (Hüber)," *Insect Biochem.*, 15:1 (1985), pp. 111–122.
Abdel–Aal and Hammock, "Transition State Analogs as Ligands for Affinity Purification of Juvenile Hormone Esterase," *Science*, 233 (Sep. 1986), pp. 1073–1076.
Bachmair and Varshavsky, "The Degradation Signal in a Short–Lived Protein," *Cell*, 45 (Mar. 1989), pp. 1019–1032.

Cheung and Hammock, "Micro–Lipid–Droplet Encapsulation of *Bacillus thuringiensis* subsp. *israelensis* δ–Endotoxin for Control of Mosquito Larvae," *Appl. & Environ. Microbiol.*, 50:4 (Oct. 1985), pp. 984–988.

Chiang and Dice, "Peptide Sequences that Target Proteins for Enhanced Degradation During Serum Withdrawal," *J. of Biol. Chem.*, 263:14 (May 1988), pp. 6797–6805.

Hammock and Sparks, "A Rapid Assay for Insect Juvenile Hormone Esterase Activity," *Analytical Biochemistry*, 82 (1977), pp. 573–579.

Hammock et al., "Expression and Effects of the Juvenile Hormone Esterase in a Baculovirus Vector," *Nature*, 344:6265 (Mar. 1990), pp. 458–461.

Hammock and Rose, "Analysis of Juvenile Hormone Esterase Activity," Chpt. 32, pp. 487–495 in Law et al. (Eds.), *Methods in Enzymology*, vol. III: *Steroids and Isoprenoids* (Part B), Academic Press (1985).

Hammock et al., "Trifluoromethylketones as Possible Transition State Analog Inhibitors of Juvenile Hormone Esterase," *Pesticide Biochem. & Physiology*, 17 (1982), pp. 76–88.

Hammock et al., "Selective Inhibition of JH Esterases from Cockroach Hemolymph," *Pesticide Biochem. & Physiology*, 7 (1977), pp. 517–530.

Hammock et al., "Strategies for the Discovery of Insect Control Agents: . . . " Chpt. 12 in Steffens et al. (Eds), *Biomechanism Regulating Growth & Development*, USDA Beltsville Symp. vol. 12, Kluwer Academic Press (1988).

Hanzlik et al., "Isolation and Sequencing of cDNA Clones Coding for Juvenile Hormone Esterase from *Heliothis virescens,*" *J. of Biol. Chem.*, 264:21 (Jul. 1989), pp. 12419–12425.

Hanzlik and Hammock, "Characterization of Affinity–purified Juvenile Hormone Esterase from *Tricholplusia ni,*" *J. Biol. Chem.*, 1987:23 (Oct. 1987), pp. 12584–13591.

(List continued on next page.)

*Primary Examiner*—Karen Cochrane Carlson
*Assistant Examiner*—Gabriele E. Bugaisky
*Attorney, Agent, or Firm*—Majestic, Parsons, Siebert & Hsue P.C.

[57] ABSTRACT

A method is provided that accelerates the rate of kill of pests such as from the order Lepidoptera. The method comprises treating the pests or their loci with at least two different insect toxins which are expressed from at least one recombinant microbe. Pairs of toxins that do not compete with each other on the same binding site and that differ in their pharmacology have been found to provide synergistic control. Preferred insecticidal microbes are baculoviruses.

9 Claims, 1 Drawing Sheet

OTHER PUBLICATIONS

Huynh et al., "Constructing and Screening cDNA Libraries in λgt10 and λgt11," Chpt. 2, IRL Press (Oxford), (1985), pp. 49–78.

Ichinose et al., Pharmacokinetic Studies of the Recombinant Juvenile Hormone Esterase in *Manduca sexta, Pesticide Biochem. & Physiology*, 42 (1992), pp. 13–23.

Ichinose et al., "Uptake of Juvenile Hormone Esterase by Pericardial Cells of *Manduca sexta*," submitted to *Insect Biochem. Molec. Biol.* (1992).

McCutchen et al., "Development of a Recombinant Baculovirus Expressing an Insect–Selective Neurotoxin: Potential for Pest Control," *Bio/Technology*, 9 (Sep. 1991), pp. 848–852.

Philpott and Hammock, "Juvenile Hormone Esterase is a Biochemical Anti–Juvenile Hormone Agent," *Insect Biochem.*, 20:5 (1990), pp. 451–459.

Rogers et al., "Amino Acid Sequences Common to Rapidly Degraded Proteins: The Pest Hypothesis," *Science*, 234 (Oct. 1986), pp. 364–368.

Sparks and Hammock, "Induction and Regulation of Juvenile Hormone Esterases During the Last Larval Instar of the Cabbage Looper, *Trichoplusia ni,*" *J. Insect. Physiolo.*, 25 (1979), pp. 551–560.

Sparks and Hammock, "Comparative Inhibition of the Juvenile Hormone Esterases from *Trichoplusia ni, Tenebrio molitor,* and *Musca domestica,*" *Pesticide Biochem. & Physiology*, 14 (1980), pp. 290–302.

Wozniak and Jones, "Immunochemical Characterization of Juvenile Hormone Esterase from Different Species of Lepidoptera," *Biochem. & Biophys. Res. Commun.*, 144:3 (May 1987), pp. 1281–1286.

Wroblewski et al., "Regulation of Juvenile Hormone Esterase Gene Expression in the Tobacco Budworm (*Heliothis virescens*)," *Archives of Biochem. & Biophys.*, 278:2 (May 1990), pp. 461–466.

Eldridge et al., "Insecticidal Properties of Genetically Engineered Baculoviruses Expressing an Insect Juvenile Hormone Esterase Gene," *Appl. & Environ. Microbiol.*, 58:5 (May 1992), pp. 1583–1591.

Hayakawa, "Structure of a Growth–Blocking Peptide Present in Parasitized Insect Hemolymph," *J. of Biol. Chem.*, 266:13 (May 5, 1991), pp. 7982–7984.

Hayakawa, "A Putative New Juvenile Peptide Hormone in Lepidopteran Insects," *Biochemical and Biophysical Research Communications*, 185:3 (Jun. 30, 1993), pp. 1141–1147.

Smith et al., "Production of Human Beta Interferon in Insect Cells Infected with a Baculovirus Expression Vector," *Mol. Cell Biol.*, 3 (1983), pp. 2156–2165.

Betana et al., "Potential of Baculo Viruses Expressing a Scorpion Toxin and an Esterase in Agriculture . . . ," *Abstr. Pap. Am. Chem. Soc.*, (206 Meet., Pt. 1, AGR0122), 1993 (Abstract only).

Hayakawa, "Juvenile Hormone Esterase Activity Repressive Factor in the Plasma of Parasitized Insect Larvae," *J. Biol. Chem.*, 265:19 (1990), pp. 10812–10816.

Hayakawa, "Juvenile Hormone Esterase Activity Repressive Peptide in the Parasitized Armyworm Hemolymph," *Zool. Sci.* (Toyko), 7:6 (1990), p. 1061 (Abstract only).

Ward et al., "Analaysis of the Catalytic Mechanism of Juvenile Hormone Esterase by Site–Directed Mutagenesis," *Int. J. Biochem.* (England), 24:12 (Dec. 1993), pp. 1933–41 (Abstract only).

Hammock et al., "Development of Recombinant Viral Insecticides by Expression of an Insect–Speicfic Toxin . . . ," *Arch. Insect Biochem. Physiol.* (US), 22:3–4 (1993), pp. 315–344 (Abstract only).

Possee et al., "Expression of the Proteins with Insecticidal Activities Using Baculo Virus Vectors . . . ," *Ann. N.Y. Acad. Sci.*, 646 (1991), pp. 234–239 (Abstract only).

Hammock et al., "Improving the Efficacy of Baculo Virus Insecticides by Expressing with Insect Selective Proteins," *Abstr. Pap. Am. Chem. Soc.* (202 Meet., Pt. 1, AGR09) (1991) (Abstract only).

Bonning et al., "Further Development of a Recombinant Baculovirus Insecticide Expressing the Enzyme JHE from Heliothis–Virescens," *Biochem. Mol. Biol.*, 22:5 (1992) pp. 453–458 (Abstract only).

Piek et al., "The Pharmacology of Microbracon Venom," *Comp. Biochem. Physiol.*, vol. 72C, pp. 303–309 (1982).

Miller et al., "Bacterial, Viral, and Fungal Insecticides," *Science*, 219, pp. 715–721, (Feb. 11, 1983).

Sakurai et al., "Complete Nucleotide Sequence of Gene for Sex–Specific Storage Protein of *Bombyx mori,*" *Nucleic Acids Research*, 16:15, pp. 7717–7718 (1988).

Merryweather et al., "Construction of Genetically Engineered Baculovirus Insecticides Containning the *Bacillus thuringiensis* subsp. *kurstaki* HD–73 Delta Endotoxin," *J. of Gen. Virol.*, 71, pp. 1535–1544 (1990).

Martens et al., "Insecticidal Activity of a Bacterial Crystal Protein Expressed by a Recombinant Baculovirus in Insect Cells," *Applied and Environmental Microbiology*, 56:9, pp. 2764–2770, (Sep. 1990).

Tomalski and Miller, "Insect Paralysis by Baculovirus–Mediated Expression of a Mite Neurotoxin Gene," *Nature*, 352, pp. 82–85, (Jul. 4, 1991).

Zlotkin, "Toxins Derived from Arthropod Venoms Specifically Affecting Insects," Chpt. 15 in *Comprehensive Insect Physiology, Biochemistry & Pharmacology*, vol. 10, pp. 499–541 (1985).

Gordon et al., "The Binding of the insect Selective Neurotoxin (AaIT) from Scorpion Venom to Locust Synaptosomal Membranes," *Biochimica et Biophysica Acta*, 778, pp. 349–358 (1984).

Stewart et al., "Construction of an Improved Baculovirus Insecticide Containing an Insect–Specific Toxin Gene," *Nature*, 352, pp. 85–88, (Jul. 4, 1991).

McCutchen et al., "Development of Surrogate Substrates for Juvenile Hormone Esterase," *Archives of Biochemistry and Biophysics*, 307:2 (Dec. 1993), pp. 231–241.

Abdel–Aal and Hammock, "Apparent Multiple Catalytic Sites Involved in the Ester Hydrolysis of Juvenile Hormones by the Hemolymph and . . . ," *Arch. Biochem. Biophys.*, 243:1, (1985), pp. 206–219.

Maeda et al., "Insectidical Effects of an Insect–Specific Neurotoxin Expressed by a Recombinant Baculovirus," *Virology*, 184 (1991), pp. 777–780.

Touhara et al., "Ligand Binding by a Recombinant Insect Juvenile Hormone Binding Protein," *Biochem.*, 32:8 (1993), pp. 2068–2075.

McCutchen et al., "Recombinant Baculovirus Expressing an Insect–selective Neurotoxin: . . . ," in *Natural & Engineered Pest Management Agents* (Hedin et al., eds), ACS Sympo. Series #551, Am. Chem. Soc., (1994) pp. 348–367.

Heinz et al., "Direct Effects of Recombinant Nuclear Polyhedrosis Viruses on Selected Non–Target Organisms," *J. Econ. Entomol.*, 88:2, (1995), pp. 259–264.

Hammock, "Recombinant Baculoviruses as Biological Insecticides," in *Pest Management: Biolgoically Based Technologies* (Lumsden and Vaughn, eds.), ACS Symp. Series, Am. Chem. Soc., (1993), pp. 313–325.

Bonning and Hammock, "Lethal Ratios: An Optimized Strategy for Presentation of Bioassay Data Generated from Genetically Engineered Baculoviruses," *J. Invert. Pathol.*, 62 (1993), pp. 196–197.

Maeda et al., "Recombinant Baculoviruses Expressing Foreign Genes for . . . ," in *Pest Control with Enhanced Environmental Safety*, (Duke et al., eds.), ACS Sympos. Series #524, Am. Chem. Soc. (1993), pp. 281–297.

Bonning and Hammock, "Development and Potential of Genetically Engineered Viral Insecticides," *Biotechnol. Genetic Engeinnering Rev.*, 10 (1992), pp. 455–489.

Hammock et al., "Cloning, Expression and Biological Activity of the JHE from *Heliothis virescens*," in *Molecular Insect Science* (Hagedorn et al., eds.), Plenum Press (1990), pp. 49–56.

Bonning et al., "Superior Expression of JHE and β–Galactosidase from the Basic Protein Promoter of *Autographa californica* Nuclear Polyhedrosis Virus Compared to the . . . ," *J. Gen. Virol.*, 75 (1994), pp. 1551–1556.

Harshman et al., "Cloning, Characterization and Genetics of the JHE Gene from *Heliothis virescens*," *Insect. Biochem. Molec. Biol.*, 24:7 (1994), pp. 671–676.

Ichinose et al., "Pharmacokinetics and Tissue Uptake of the Recombinant JHE in Insects" in *Pesticides/Environment: . . .* , (Mitsui et al., eds.), Proc. of 1st Int'l. Symp. on Pest. Sci., Pesticide Sci. Soc. of JP (1993).

Bonning et al., "Insect Control by Use of Recombinant Baculoviruses Expressing JHE," in *Natural and Engineered Pest Management Agents* (Hedin et al., eds.), ACS Symp. Ser. #551, Am. Chem. Soc. (1994), pp. 368–383.

Roelvink et al., "Dissimilar Expression of *Autographa californica* Multiple Nucleocapsid Nuclear Polyhedrosis Virus Polyhedrin and p10 Gene," *J. Gen. Virol.*, 73 (1992), pp. 1481–1489.

Booth et al., Localization of JHE During Development in Normal and in Recombinant Baculovirus–Infected Larvae of the Moth *Trichoplusia ni*, *Tissue & Cell*, 24:2 (1992), pp. 267–282.

Harshman et al., "Effects of Recombinant Juvenile Hormone Esterase on *Aedes aegypti*," *Proc. Calif. Mosq. Vector Control Assoc.*, (1991), pp. 77–80.

Hammock, "Regulation of Juvenile Hormone Titer: Degradation," in *Comprehensive Insect Physiology, Biochemistry, and Pharmacology* (Kerkut and Gilbert, eds.) Pergamon Press (1985), pp. 431–472.

Jones and Hammock, "Prepupal Regulation of Juvenile Hormone Esterase through Direct Induction by Juvenile Hormone," *J. Insect Physiol.*, 29:6, (1983), pp. 471–475.

Sparks and Hammock, "A Comparison of the Induced and Naturally Occurring Juvenile Hormone Esterases from Last Instar Larvae of *Trichoplusia ni*," *Insect Biochem.*, 9, (1979), pp. 411–421.

Sparks et al., Effects of the Anti Hormone—Hormone Mimic ETB on the Inductio nof Insect Juvenile Hormone Esterase in *Trichoplusia ni*, *Life Sci.*, 25 (1979), pp. 445–450.

Zlotkin et al., "The Effect of Scorpion Venom on Blowfly Larvae—A New Method for the Evaluation of Scorpion Venoms Potency," *Toxicon*, 9 (1971), pp. 1–8.

Zlotkin et al., "An Excitatory and a Depressant Insect Toxin from Scorpion Venom both Affect Sodium Conductance and Possess a Common Binding Site," *Arch. Biochem. & Biophys.*, 240:2 (Aug. 1985), pp. 877–887.

Adachi et al., "cDNA Structure and Expressio nof Bombyxin, an Insulin–like Brain Secretory Peptide of the Silkworm *Bombyx mori*," *J. Biol. Chem.*, 264:13 (1984), pp. 349–358.

Maeda, Increased Insecticidal Effect by a Recombinant Baculovirus Carrying a Synthetic Diuretic Hormone Gene, *Biochem. & Biophys. Res. Comm.*, 165:3 (1989), pp. 1177–1183.

Carbonell et al., "Synthesis of a Gene Coding for an Insect–Specific Scorpion Neurotoxin and Attempts to Express it Using Baculovirus Vectors," *Gene*, 73, pp. 409–418 (1988).

Carbonell et al., "Baculovirus Interaction with Nontarget Organisms: a Virus–Borne Reporter Gene is Not Expressed in Two Mammalian Cell Lines," *Appl. Environ. Microbiol*, 53:7 (Jul. 1987), pp. 1412–1417.

Dee et al., "Expression and Secretion of a Functional Scorpion Insecticidal Toxin in Cultured Mouse Cells," *Bio/Technology*, 8, (Apr. 1990), pp. 339–342.

Cameron et al., "Insect Cell Culture Technology in Baculovirus Expression Systems," *Trends in Biotechnology*, vol. 7, (1989), pp. 66–70.

Moffat, Anne Simon, "New Chemicals Seek to Outwit Insect Pests," *Science*, 261, pp. 550–551 (1993).

Wang et al., "Baculovirus Vectors for Multiple Gene Expression and for Occluded Virus Production," *Gene*, 100, (1991), pp. 131–137.

Zlotkin et al., "Functional Duality and Structural Uniqueness of Depressant Insect–Selective Neurotoxins," *Biochemistry*, 30, (1991), pp. 4814–4821.

Gordon et al., "Localization of Receptor Sites for Insect–Selective Toxins on Sodium Channels by Site–Directed Antibodies," *Biochemistry*, 31 (1992), pp. 7622–7628.

Eitan et al., "A Scorpion Venom Neurotoxin Parlytic to Insects that Affects Sodium Current Inactivation: Purification, Primary Structure, and Mode of Action," *Biochemistry*, 29, (1990), pp. 5941–5947.

Trainer et al., "Neurotoxin Binding and Allosteric Modulation at Receptor Sites 2 and 5 on Purified and Reconstituted Rat Brain Sodium Channels," *J. Biol. Chem.*, 268:23, pp. 17114–17119 (1993).

Antkiewicz–Michaluk, Lucyna, "Receptor and Voltage–Operated Ion Channels in the Central Nervous System," *Pol. J. Pharmacol.*, 47, pp. 253–264 (1995).

Adams et al., "Two Classes of Channel–Specific Toxins from Funnel Web Spider Venom," *J. Comp. Physiol. A*, 164, pp. 333–342 (1989).

Olivera et al., "Neuronal Calcium Channel Antagonists. Discrimination Between Calcium Channel Subtypes Using ω–Conotoxin from *Conus magus* Venom," *Biochemistry*, 26, pp. 2086–2099 (1987).

Lazarovici et al., "Insect Toxic Components from the Venom of a Chactoid Scorpion, *Scorpio maurus palmatus* (Scorpionidae)," *J. Biol. Chem.*, 257:14, pp. 8397–8404 (1982).

AGA TCT GGA TCC ATG AAG ATC CTC CTT GCT ATT GCC CTT ATG
TCT AGA CCT AGG TAC TTC TAG GAG GAA CGA TAA CGG GAA TAC

CTT AGC ACC GTG ATG TGG GTG AGC ACC GGC GTG CGC GAC GCC
GAA TCG TGG CAC TAC ACC CAC TCG TGG CCG CAC GCG CTG CGG

TAC ATC GCC GAC GAC AAG AAC TGC GTG TAC ACC TGC GGC GCC
ATG TAG CGG CTG CTG TTC TTG ACG CAC ATG TGG ACG CCG CGG

AAC TCT TAC TGC AAC ACC GAC TGC ACC AAG AAC GGC GCC GAC
TTG AGA ATG ACG TTG TGG CTC ACG TGG TTC TTG CCG CGG CTG

TCT GGC TAC TGC CAA TGG TTC GGC AAA TAC GGC AAC GCA TGC
AGA CCG ATG ACG GTT ACC AAG CCG TTT ATG CCG TTG CGT ACG

TGG TGC ATC AAA CTT CCC GAC AAA GTG CCC ATC CGC ATT CCC
ACC ACG TAG TTT GAA GGG CTG TTT CAC GGG TAG GCG TAA GGG

GGC AAA TGC CGC TAA GGA TCC AGA TCT GAG CTC
CCG TTT ACG GCG ATT CCT AGG TCT AGA CTC GAG

Fig._1

```
                         SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
         (A) LENGTH: 285 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

AGATCTGGAT CCATGAAGAT CCTCCTTGCT ATTGCCCTTA TGCTTAGCAC CGTGATGTGG      60

GTGAGCACCG GCGTGCGCGA CGCCTACATC GCCGACGACA AGAACTGCGT GTACACCTGC     120

GGCGCCAACT CTTACTGCAA CACCGACTGC ACCAAGAACG GCGCCGACTC TGGCTACTGC     180

CAATGGTTCG GCAAATACGG CAACGCATGC TGGTGCATCA AACTTCCCGA CAAAGTGCCC     240

ATCCGCATTC CCGGCAAATG CCGCTAAGGA TCCAGATCTG AGCTC                     285

(2) INFORMATION FOR SEQ ID NO:2:

(i) SEQUENCE CHARACTERISTICS:
         (A) LENGTH: 65 amino acids
         (B) TYPE: amino acid
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:2:

Gly Val Arg Asp Ala Tyr Ile Ala Asp Asp Lys Asn Cys Val Tyr Thr
1               5                  10                  15

Cys Gly Ala Asn Ser Tyr Cys Asn Thr Glu Cys Thr Lys Asn Gly Ala
                20                  25                  30

Glu Ser Gly Tyr Cys Gln Trp Phe Gly Lys Tyr Gly Asn Ala Cys Trp
            35                  40                  45
```

```
Cys Ile Lys Leu Pro Asp Lys Val Pro Ile Arg Ile Pro Gly Lys Cys
    50                  55                  60

Arg
65

(2) INFORMATION FOR SEQ ID NO:3:

(i) SEQUENCE CHARACTERISTICS:
        (A) LENGTH: 67 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

Gly Val Arg Asp Gly Tyr Ile Ala Gln Pro Glu Asn Cys Val Tyr His
1               5                   10                  15

Cys Phe Pro Gly Ser Pro Gly Cys Asp Thr Leu Cys Lys Gly Asp Gly
            20                  25                  30

Ala Ser Ser Gly His Cys Gly Phe Lys Glu Gly His Gly Leu Ala Cys
            35                  40                  45

Trp Cys Asn Asp Leu Pro Asp Lys Val Gly Ile Ile Val Glu Gly Glu
        50                  55                  60

Lys Cys His
65
```

INSECT CONTROL WITH MULTIPLE TOXINS

This is a division of application Ser. No. 08/435,040, filed May 8, 1995, U.S. Pat. No. 5,756,340.

This invention was made with government support under Grant No. 91-37302-6185, awarded by the United States Department of Agriculture. The U.S. Government has certain rights in the invention.

FIELD OF THE INVENTION

The present invention generally relates to uses of insect toxins in controlling insects, and more particularly to insecticidal recombinant microbes expressing insect-selective toxins in synergistic combinations to magnify insect kill rate.

BACKGROUND OF THE INVENTION

The lepidopteran family Noctuidae includes some of the most destructive agricultural pests, such as the genera Heliothis, Helicoverpa, Spodoptera, and Trichoplusia. For example, included in this family are the tobacco budworm (*Heliothis virescens*), the cotton bollworm (*Helicoverpa zea*), the cotton leafworm (*Alabama argillacea*), the spotted cutworm (*Amathes niarum*), the glassy cutworm (*Crymodes devastator*), the bronzed cutworm (*Nephelodes emmedonia*), the fall armyworm (*Laphygma frugiperda*), the beet armyworm (*Spodoptera exigua*), and the variegated cutworm (*Peridroma saucia*).

Resistance of agricultural pests, such as the Noctuidae (and others), to pesticides leads to environmental and human health risks. This problem of insecticide resistance leads to the use of more non-selective and toxic compounds, in order to overcome pest resistance. This creates a destructive and vicious cycle.

Selective natural toxins have been suggested for use in insect control. These toxins include substances which are produced in specialized glandular tissues in the body of a venomous animal. The venom may be introduced into the body of its prey or opponent, such as by the aid of a stinging-piercing apparatus, in order to paralyze and/or kill it, although other means of delivering venom are known. Scorpions, for example, contain in their venom a number of proteins, or neurotoxins, which are toxic and act on the excitable systems. Among the insect specific toxins suggested for use in insect control are toxins from *Bacillus thuringiensis* from the scorpions *Buthus eupeus* and *Androctonus australis, Leiurus quinqustriatus hebraeus, Leiurus quinqustriatus quinqustriatus*, and from the mite *Pyemotes tritici*.

The venoms derived from scorpions belonging to the Buthinae subfamily have four main groups of polypeptide neurotoxins which modify axonal sodium conductance. One group of scorpion neurotoxins are the α-toxins, which selectively affect mammals through an extreme prolongation of the action potentials due to a slowing or blockage of the sodium channel inactivation (Catterall, *Science*, 223:653–661 (1984); Rochat et al., *Advances in Cytopharmacology*, pp. 325–334 (1979)). The second group of toxins, the β-toxins, affect sodium channel activation (Couraud and Jover in *Handbook of Natural Toxins* (Tu, A. Ed.) Vol. 2, pp. 659–678 (1984) New York: Marcel Dekker. The third group of neurotoxins are the depressant insect selective toxins which induce a progressively developing flaccid paralysis of insects by the blockage of action potentials substantially due to the suppression of sodium current (Lester et al., *Biochim. Biophys. Acta*, 701:370–381 (1982); Zlotkin et al., *Arch. Biochem. Biophys.*, 240:877–887 (1985)). The fourth group of neurotoxins are the excitatory insect selective toxins which cause an immediate (knock down) spastic paralysis of insects by the induction of repetitive firing in their motor nerves due to an increase of the sodium peak current and the voltage dependent slowing of its inactivation (Walther et al., *J. Insect Physiol.*, 22:1187–1194 (1976); Pelhate et al., *J. Physiol.*, 30:318–319 (1981)).

In addition to scorpion and mite toxins, other insect-selective toxins have been identified in venoms from snails, spiders, and a number of other arthropods. [See review by Zlotkin, *Comprehensive Insect Physiology, Biochemistry and Pharmacology*, Vol. 10, Chapter 15, pp. 499–541 (1985).] The venoms of braconid wasps are highly toxic to lepidopterous larvae. The venom of the braconid Bracon hebetor causes a flaccid paralysis in lepidopterous larvae by inducing presynaptic interruption of the excitatory glutaminergic transmission at the insect neuromuscular junction (Piek et al., *Comp. Biochem. Physiol.*, 72C:303–309 (1982)). The venoms of solitary wasps are toxic to a large number of insects and spiders from different orders (Rathmeyer, *Z. Vergl. Physiol.*, 45:453–462 (1962)). An example of these venoms is the venom of *Philanthus triangulum* which induces in insects a flaccid paralysis substantially due to presynaptic blockage of neuromuscular transmission; this venom affects both excitatory and inhibitory transmission (May et al., *Insect Physiol.*, 25:285–691 (1979)). The venom of the black widow spider, *Latrodectus mactans*, contains components which are neurotoxic to insects, but not to mammals, and other components with the opposite selectivity (Fritz et al., *Nature*, 238:486–487 (1980); Ornberg et al., *Toxicon*, 14:329–333 (1976)).

More recently, a toxin designated as LqhαIT, which strongly reassembles α toxins in its primary structure and electrophysiological effects, was isolated from the venom *L. quinquestriatus* hebraeus and was shown to affect mainly insects (Eitan et al., *Biochemistry*, 29 (1990), pp. 5941–5947).

The venom of venomous animals is composed of a variety of toxins affecting different target sites in the excitable systems of the prey. On the basis of the data comparing the activity of toxins and their respective crude venom towards lepidopterous larvae it is clear that the potency of the crude venom cannot be explained by the activity of one toxin alone. The higher potency of the crude venom could be related to a cooperativity among different toxins in the venom affecting different target sites on the same ionic channels (Table 3, Trainer et al., JBC, 268, 17114–17119 (1993)), different ionic channels on the same excitable cells (Olivera et al., *Science*, 249, 257–263 (1990)), and/or different binding sites on adjacent excitable cells (nerves and/or muscles) (Olivera et al., *Science*, 249, 257–263 (1990)).

The depressant and the excitatory insect-selective toxins do not compete with the α insect toxin for its binding site (Gordon and Zlotkin, *FEBS Lett.*, 315 (1993), pp. 125–128). In contrast to locust or cockroach neuronal membranes the excitatory toxins do not displace the depressant toxins from their binding sites in neuronal membranes of lepidopterous larvae (Gordon et al., *Biochemisty*, 31 (1992), pp. 76-22–7628; Moskowitz et al., *Insect Biochem. Molec. Biol.*, 24 (1994), pp. 13–19).

Recently, the nuclear polyhedrosis virus *Autographa californica* (AcNPV), from the family Baculoviridae, has been genetically modified for an increased speed of kill by expressing insect-selective toxins. The introduction of an insect-selective toxin into an insect-pathogenic virus has resulted in a reduction in the killing time of insect hosts, as is described by U.S. Ser. No. 08/229,417, filed Apr. 15, 1994, which is a continuation-in-part application of U.S. Ser. No. 07/629,603, filed Dec. 19, 1990, having (in part) common assignment herewith.

Tomalski et al., U.S. Pat. No. 5,266,317, issued Nov. 30, 1993, discuss use of recombinant baculoviruses that express an insect-specific paralytic neurotoxin of an insect predacious mite. Barton et al., U.S. Pat. No. 5,177,308, issued Jan. 5, 1993, take a different approach in creating transgenic plants that express a scorpion derived insect-specific toxin and/or a soil dwelling microorganism toxin. In a copending application, of common assignment herewith, Hammock and McCutchen, Ser. No. 08/279,956, filed Jul. 5, 1994, discuss insect control with a synergistic combination of recombinant virus and an organic insecticide.

These newly emerging tools using recombinant strategies to control insect pest populations hold promise particularly since the wide-scale presence of pest resistance to organic insecticides, such as pyrethroids, has begun to result in substantial crop losses. In cotton alone, the presence of pyr-R Heliothis species has begun to result in millions of lost dollars annually. In fact, in several cases pyrethroid insecticides have completely failed to control infestations of Heliothis larvae in cotton, which has resulted in complete destruction of the crop.

SUMMARY OF THE INVENTION

In one aspect of the present invention, a method for controlling a variety of pests is provided through use of genetically engineered, insecticidal microbes. Pests controlled in accordance with the invention are, for example, from the group insects, acarids, and nematodes. Thus, the invention is applicable to the Lepidoptera as well as other orders, and to the Noctuiidae as well as other families. Such pests are treated (or their loci treated) with a synergistic combination of toxins expressed by one or more recombinant microbes.

For example, the method may use a combination of first recombinant pathogen that expresses a first neurotoxin and a second recombinant pathogen that expresses a second neurotoxin, or may use a single recombinant virus expressing a plurality (such as the first and second) of neurotoxins. The inventive method accelerates the rate of kill of pests by the virus.

BRIEF DESCRIPTION OF DRAWING

In the drawing, FIG. 1 illustrates the nucleotide sequence of a synthetic gene of LqhIV, SEQ ID NO:1, which one of the preferred toxins for practicing the invention.

DETAILED DESCRIPTION OF THE PREFERRED EMBODIMENTS

The present invention is the use of genetically engineered, insecticidal microbes in combinations to treat pests such as insects. Although recombinant baculoviruses will be used throughout as an illustration of preferred microbes, this invention can be practiced with a variety of microbes as recombinant delivery systems. Thus the microbes useful in the present invention include DNA and RNA viruses, such as baculoviruses, fungi and bacteria.

On the order of forty nuclear polyhedrosis viruses have been isolated from insect species. (See, for example, *Atlas of Invertebrate Viruses*, Adams and Bonami, editors, CRC Press, Inc., 1991.) Various baculoviruses, including those that infect cotton bollworm, *Helicoverpa zea*, tobacco budworm, *Heliothis virescens*, Douglas fir tussock moth, *Orgia pseudotsugata*, gypsy moth, *Lymantria dispar*, alfalfa looper, *Autographa californica*, European pine fly, *Neodiiprion sertifer*, and codling moth, *Laspeyresia pomonella*, have been registered as pesticides and all such baculoviruses from insect species are suitable for practicing the invention.

Numerous fungi are capable of infecting insects. Introduction of the insect-selective toxin into the genome of such fungi could enhance the potency as pesticides. For example, *Beauvaria bassania* and *Beauvaria brongniartii* have a wide host range and have been suggested as candidates for microbial pesticides (see review by Miller et al., *Science*, 219:715–721, 1983).

Bacteria (other than *Bacillus thuringiensis*) that have been considered as insect control agents include *Bacillus popilliae, B. lentimorbus*, and *B. sphaericus*. Their potential as pesticides can be enhanced by improving their potency through the incorporation of an insect-selective toxin into their genome.

Practice of the invention involves the combined use of two, synergistically acting toxins in controlling insects. These two can be expressed by means of a single recombinant microbe in which both toxin genes have been introduced, or may be practiced by preparing two recombinant microbes, each of which has been constructed by cloning a gene encoding the respective insect toxins into the genome. The combinations of toxin pairs selected are determined in several ways. As will be described hereinafter (as is described by the screening techniques of Example 6), one preferably selects toxins that act at the same cellular channels (typically sodium channels) but at non-overlapping sites, as will be further described hereinafter.

As earlier mentioned, preferred insecticidal microbes for practicing the invention are baculoviruses. By "baculovirus" is meant any baculovirus of the family Baculoviridae, such as a nuclear polyhedrosis virus (NPV). Baculoviruses are a large group of evolutionarily related viruses, which infect only arthropods; indeed, some baculoviruses only infect insects that are pests of commercially important agricultural and forestry crops, while others are known that specifically infect other insect pests. Because baculoviruses infect only arthropods, they pose little or no risk to humans, plants, or the environment.

Of the suitable DNA viruses, in addition to the Baculoviridae are the entomopox viruses (EPV), such as *Melolontha melonotha* EPV, *Amsacta moorei* EPV, *Locusta migratoria* EPV, *Melanoplus sanguinipes* EPV, *Schistocerca gregaria* EPV, *Aedes aogypti* EPV, and *Chironomus luridus* EPV. Other suitable DNA viruses are granulosis viruses (GV). Suitable RNA viruses include togaviruses, flaviviruses, picornaviruses, cytoplasmic polyhedrosis viruses (CPV), and the like. The subfamily of double stranded DNA viruses Eubaculovirinae includes two genera, NPVs and GVs, which are particularly useful for biological control because they produce occlusion bodies in their life cycle. Examples of GVs include *Cydia pomonella* GV (coddling moth GV), *Pieris brassicae* GV, *Trichoplusia ni* GV, *Artogeia rapae* GV, and *Plodia interpunctella* GV (Indian meal moth).

Suitable baculoviruses for practicing this invention may be occluded or non-occluded. The nuclear polyhedrosis viruses ("NPV") are one baculovirus sub-group, which are "occluded." That is, a characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, and *Rachiplusia ou* NPV. For field use occluded viruses often are preferable due to their greater stability since the viral polyhedrin coat provides protection for the enclosed infectious nucleocapsids.

Among illustrative, useful baculoviruses in practicing this invention are those *Anagrapha falcifera, Anticarsia gemmatalis, Buzura suppressuria, Cydia pomonella, Helicoverpa zea, Heliothis armigera, Manestia brassicae, Plutella xylostella, Spodoptera exigua, Spodoptera littoralis,* and *Spodoptera litura*. A particularly useful "NPV" baculovirus for practicing this invention is AcNPV, which is a nuclear polyhedrosis virus from *Autographa californica*. *Autographa californica* is of particular interest because various major pest species within the genera Spodoptera, Trichoplusia, and Heliothis are susceptible to this virus.

The expressed insecticidal toxins are particularly a neurotoxin derived from or similar to an arthropod or other invertebrate toxin, such as a scorpion toxin, a wasp toxin, a snail toxin, a mite toxin, or a spider toxin. A useful scorpion toxin is, for example, AaIT from *Androctonus australis*. Zlotkin et al., *Biochimie*, 53, 1073–1078 (1971). A useful snail venom is that from the snail *Conus querciones*, which the animal delivers by mouth and some individual toxins of which appear to be selective for arthropods including insects. See, for example, Olivera et al., "Diversity of Conus Neuropeptides," *Science*, 249:257–263 (1990).

Even peptides that normally appear in an insect's developmental life can operate as an insecticidal toxin, and be used in accordance with this invention. For example, the precocious appearance of juvenile hormone esterase ("JHE") will reduce juvenile hormone titers in a host insect, which typically results in irreversible termination of the feeding stage, attempted pupation, and death of the pest insect. The amino acid sequence of JHE is known, and the gene has been cloned. Preferred embodiments of the present invention include recombinant microbes expressing juvenile hormone esterase (JHE) mutations, and exemplary methods for preparing such JHE mutations or deletions, several useful JHE mutations, and recombinant expression vectors for use in controlling insects (having JHE or mutated JHE coding sequences) as are described by WO 94/03588, published Feb. 17, 1994, inventors Hammock et al., incorporated herein by reference.

Two mutants described in the Hammock et al. WO 94/03588 are a double lysine mutant (K29R, K522R) where the normal lysines of JHE at position 29 and position 522 were changed to arginine by site-directed mutagenesis. Another mutant described was where serine 201 was changed to glycine and the mutant designated "S201G." The insecticidal activity of the catalytically deficient S201G mutant of JHE provided similar time for 50% death of test insects to scorpion toxins (when engineered in AcNPV). Thus, the naturally occurring JHE insect protein, which is not normally toxic, can be modified by means such as site-directed mutagenesis (or otherwise) to a toxic agent. In addition to amino acid residue changes, other JHE mutants could be prepared such as by deleting the N-terminal 19 amino acids, which are a signal sequence for the newly made protein to enter the secretory pathway, become glycosolated, and exit the cell.

As with JHE, the amino acid sequence of the excitatory toxin from *Androctonus australis* (AaIT) has also been determined, the sequence has been published (Darbon 1982), and the AaIT gene has been cloned and inserted into expression vectors for insect control. (See WO 92/11363, published Jul. 9, 1992, inventors Belagaje et al.) The AaIT toxin exhibits toxicity to insects, while being non-toxic to isopods and mammals.

Yet another suitable toxin for practicing the invention affects insect sodium channels in a manner very similar to the effect of α-toxins on mammalian sodium channels. This neurotoxin was derived from a yellow scorpion *Leuirus quinquestriatus hebraeus*, and is called herein LqhαIT. The identification and purification of this toxin was described in "A Scorpion Venom Neurotoxin Paralytic to Insects that Affects Sodium Current Inactivation: Purification, Primary Structure, and Mode of Action," published by Eitan et al., *Biochemistry*, 29:5941–5947 (1990).

Two preferred toxins for practicing the invention are novel in isolated and purified form, and will be described more fully hereinafter. Briefly, these two are designated "LqhIV" and "LqhVI." These two toxins occur in the venom of *L. quinqestriatus hebraeus*, which contains a number of individual toxins in admixture in the native form. The LqhIV toxin is an extremely potent lepidopterous toxin, shows positive cooperativity with other scorpion toxins when injected into the Lepidopterous larvae, and has no or weak mammal toxicity. A synthetic gene for this LqhIV toxin is illustrated by FIG. 1, SEQ ID NO:1.

Thus, the genes for these two preferred toxins can be synthesized (since the peptide sequence sizes are sufficiently small so as to make feasible synthesizing the DNA). Alternatively, the genes can be cloned. The coding sequences may than be cloned into a transfer vector, as will be exemplified further hereinafter.

We have demonstrated aspects of the invention with the synergistic combination of the toxins AaIT and LqhαIT in both blow fly larvae and in Heliothis larvae where the insecticidal activity of these insect-selective neurotoxins was increased five to ten fold when used in combination. Other combinations illustrating the invention and experimental details will be more fully discussed hereinafter.

Various other scorpion toxins (e.g. the Buthoid scorpion) can also be used for the synergistic combinations, such as LqqIT2, which is a depressive insect toxin from *Leiurus quinquestriatus quinquestriatus*. The purification method used to obtain this neurotoxin was published by Zlotkin et al., *Archives of Biochem. Biophys.*, 240:877–887 (1985).

BjIT2 is another depressive insect toxin and is from *Buthotus judaicus*. The purification has been published in Lester et al., *Biochim. Biophys. Acta*, 701:370–381 (1982). BjIT2 exists in two isoforms which differ in amino acid sequence at position 15. Form 1 has isoleucine in this position while form 2 has valine.

LqhIT2 is yet another depressive insect toxin from *Leiurus quinquestriatus hebraeus* which was purified using reverse phase HPLC.

Yet other toxins, purified from the venom of the chactoid scorpion, *Scorpio maurus palmatus*, can also be used. For example, SmpIT2, from the chactoid scorpion, *Scorpio maurus palmatus*, is a depressive insect toxin. Its purification is described in Lazarovici et al., *J. Biol. Chem.*, 257:8397–8404 (1982).

Still other toxins purified from the venom of the chactoid scorpion, *Scorpio maurus palmatus*, are SmpCT2 and SmpCT3, and crustacean toxins, whose purification has been described in Lazarovici, Ph.D. thesis (1980), Hebrew University, Jerusalem, "Studies on the Composition and Action of the Venom of the Scorpion *Scorpio maurus palmatus* (Scorpionidae)."

Table 1 lists some preferred toxins for practicing this invention along with citations to their purification and characterization.

TABLE 1

| ILLUSTRATIVE TOXINS | REFERENCES |
| --- | --- |
| AaIT | Zlotkin et al., Biochim, 53, 1075–1078 (1971). |
| AaIT$_1$ | Loret et al., Biochem., 29, 1492–1501 (1990). |
| AaIT$_2$ | Loret et al., Biochem., 29, 1492–1501 (1990). |
| LqqIT$_1$ | Zlotkin et al., Arch. f Biochem. & Biophys., 240, 877–887 (1985). |
| BjIT$_1$ | Lester et al., Biochem. Biophys. Acta, 701, 370–387 (1982). |
| LqhIT$_2$ | Zlotkin et al., Biochem., 30, 4814–4821 (1991). |
| LqqIT$_2$ | Zlotkin et al., Arch. f Biochem. & Biophys., 240, 877–887 (1985). |
| BjIT$_2$ | Lester et al., Biochem. Biophys. Acta, 701, 370–387 (1982). |
| LqhαIT | Eitan et al., Biochem., 29, 5941–5947 (1990). |
| Ts$_{VII}$ | Bechis et al., Biochem. Biophys. Res. Comm., 122, 1146–1153 (1984). |
| Mite toxin | Tomalski et al., Toxicon, 27, 1151–1167 (1989). |
| α-conotoxins | Gray et al., JBC, 256, 4734–4740 (1981); Gray et al., Biochem., 23, 2796–2802 (1984). |
| μ-conotoxins | Cruz et al., JBC, 260, 9280–9288 (1989); Crus et al., Biochem., 28, 3437–3442 (1989). |
| chlorotoxin | Debin et al., Am. J. Physiol., 264, 361–369 (1993). |
| ω-conotoxins | Olivera et al., Biochem., 23, 5087–5090 (1984); Rivier et al., JBC, 262, 1194–1198 (1987). |
| PLTX1 | Branton et al., Soc. Neurosci. Abs., 12, 176 (1986). |
| PLTX2 | Branton et al., Soc. Neurosci. Abs., 12, 176 (1986). |
| PLTX3 | Branton et al., Soc. Neurosci. Abs., 12, 176 (1986). |
| Ag1 | Kerr et al., Soc. Neurosci. Abs., 13, 182 (1987); Sugimori et al., Soc. Neurosci. Abs., 13, 228 (1987). |
| Ag2 | Kerr et al., Soc. Neurosci. Abs., 13, 182 (1987); Jackson et al., Soc. Neurosci. Abs., 13, 1078 (1987). |
| ω-Agatoxin | Adams et al., JBC, 265, 861–867 (1990). |
| μ-Agatoxin | Adams et al., JBC, 265, 861–867 (1990). |
| HoI | Bowers et al., PNAS, 84, 3506–3510 (1987). |
| α-Laterotoxin | Grasso, in Neurotoxins in Neurochemistry, ed. Dolly, 67–79 (1988). |
| Steatoda toxin | Cavalieri et al., Toxicon, 25, 965–974 (1987). |
| Bom III | Vargas et al., Eur. J. Biochem., 162, 589–599 (1987). | cDNA libraries for many of the organisms from which the Table 1 illustrative toxins can be purified are available as described by: zilberberg et al. (1992), *Insect Biochem. Molec. Biol*, 22(2), 199–203 (*Leiurus quinquestriatus hebraeus*); Gurevitz et al. (1990) *Febs Lett.*, 269(1), 229–332 (*Buthus judaicus*); Bougis et al. (1989), JBC, 264(32), 19259–19256 (*Androctonus australis*); Martin-Euclaire et al. (1992) *Febs. Lett.*, 302(3), 220–222 (*Tityus serrulatus*); Woodward et al. (1990) *EMBO J.*, 9(4), 1015–1020 (*Conus textile*); and Colledge et al. (1992) *Toxicon*, 30(9), 1111–11116 (*Conus geographus*). For others, one may construct synthetic genes coding for the toxins, in a manner analogous to that exemplified by Example 7.

As earlier mentioned, two toxins suitable for use in practicing the present invention are novel in their isolated and purified form. One of these is designated "LqhIV," and has the amino acid sequence shown as SEQ ID NO:2: GVRDAYIADD KNCVYTCGAN SYCNTECTKN GAES-GYCQWF GKYGNACWCI KLPDKVPIRI PGKCR. The SEQ ID NO:2 sixty-five amino acid peptide is further described in Example 5.

Another novel toxin, designed "LqhVI," has the amino acid sequence given by SEQ ID NO:3: GVRDGYIAQP ENCVYHCFPG SPGCDTLCKG DGASSGHCGF KEGH-GLACWC NDLPDKVGII VEGEKCH. This sixty-seven amino acid peptide is also further described by Example 5.

The toxins, such as the preferred toxins listed in Table 1, or as SEQ ID NOS:2 and 3, may be selected to form synergistic combinations most easily by first making experimental combinations of toxins having different pharmacologies. For example, AaIT is an excitatory insect toxin while LqhIT$_2$ is a depressant toxin. By routine binding protocols (see, e.g. Gordon et al., *Biochim. Biophys. Acta*, 778, 349–358 (1984) for AaIT, BJIT$_1$, and BjIT$_2$ with locust *Locusta migratoria* membrane vesicles), one screens for activity at the same channel but at non-overlapping sites for the particular insect of interest. This is because, as known to the art, there is a variability among various insect neuronal membranes. For example, several recent articles have reported that unlike locust or cockroach neuronal membranes, Lepidopterous larvae neuronal membranes can bind the depressant and excitatory insect toxins at the same time.

In the earlier noted example of a synergistic combination of AaIT and LqhαIT, there was twice the synergistic potency for the combination towards blow fly larvae than to Heliothis larvae. In contrast, with the combination of AaIT and LqhIT$_2$, there is a synergistic combination (potency of five times) when applied to Heliothis larvae, but no increased potency with respect to each toxin by itself when applied to blow fly larvae. These combinations of toxins can be used to enhance selectivity within insect groups.

For producing recombinant microbes, such as baculoviruses, for the purpose of controlling insects, a secretion signal sequence is preferably included. Secretion signal sequences may be derived from proteins of bacteria, yeast, fungi, or higher eukaryotes, including both animals and plants (for examples, see Watson, *Nucl. Ac. Res.*, 12:5145–5164 (1984). More preferred are secretion signal sequences from proteins of insect origin, for example those of cecropin B from *Hyalophora cecropia* (van Hofsten et al., *PNAS*, 82:2240–2243 (1985)), and the eclosion hormone from *Manduca sexta* (Horodyski et al., *PNAS*, 86:8123–8127 (1989)). Also preferred are the secretion signal sequences naturally associated with scorpion toxins, which can be determined by the analysis of mRNA, cDNA, or genomic DNA. More preferred is the natural secretion signal sequence of AaIT (Bougis et al., *J. Biol. Chem.*, 264:19259–19265 (1989)).

The toxins of the recombinant microbes may be expressed as functional derivatives of the toxin. A "functional derivative" of the toxin is a compound which possesses a biological activity (either functional or structural) that is substantially similar to a biological activity of the toxin. The term "functional derivative" is intended to include the "fragments," "variants," "analogues," or "chemical derivatives" of a molecule. By a "fragment" of a molecule such as a toxin is meant to refer to any polypeptide subset of the molecule. A "variant" of a molecule such as a toxin is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analog" of a molecule such as the toxin is meant to refer to a molecule substantially similar in function to either the entire molecule or to a fragment thereof. As used herein, a molecule is said to be a "chemical derivative" of another molecule when it contains additional chemical moieties not normally a part of the molecule.

Such moieties may improve the molecule's solubility, absorption, biological half-life, etc. Moieties capable of mediating such effects are disclosed in Remington's Pharmaceutical Sciences (1980). Procedures for coupling such moieties to a molecule are well known in the art.

Expression of the toxin (or toxins) will, in general, include a promoter region sufficient to direct the initiation of RNA synthesis. One baculovirus promoter gene is that coding for polyhedrin, since the polyhedrin protein is one of the most highly expressed eucaryotic genes known, although other promoter and hybrid promoter sequences may be used, for example, such as p10.

Recombinant baculoviruses expressing one toxin nay be prepared by protocols now known to the art (e.g. Tomalski et al., U.S. Pat. No. 5,266,317, exemplifying neurotoxins from the insect-parasitic mites; McCutchen et al., *Bio/Technology*, 9, 848–852 (1991) and Maeda et al., "Insecticidal Effects of an Insect-Specific Neurotoxin Expressed by a Recombinant Baculovirus," *Virology*, 184, 777–780 (1991), illustrating construction of a recombinant baculovirus expressing AaIT).

Preparation of a single baculovirus capable of expressing two different toxins may by protocols analogous to: Belayev and Roy, *Nucleic Acid Research*, 21:5, 1219–1223 (1993); Wang et al., *Gene*, 100, 131–137 (1991), with appropriate modifications. Example 1 illustrates such an analogous protocol.

EXAMPLE 1

Two insect toxin genes may be cloned into a transfer vector such as PacUW51P2 using standard molecular cloning techniques. This transfer vector is an *Autographa californica* (AcNPV) polyhedron locust-based vector that contains a copy of the AcNPV p10 promoter and SV40 transcription termination signals inserted in tandem, upstream of the polyhedron gene promoter, but in opposite orientation. This facilitates the assertion of one foreign gene coding region at a Bam HI site under the control of the polyhedron promoter, and a second foreign gene coding region at a BglII cloning site, under the control of the p10 promoter. Thus, the resulting recombinant virus expresses two foreign proteins. The recombinant AcNPV thus prepared may be isolated by propagating *Spodoptera frugiperda* cells (Sf21), which are co-transfected by calcium precipitation with the recombinant plasmid. Polyhedron-infected cells can be identified and collected post infection and the recombinant virus plaque purified by screening.

Purification of the recombinant virus may be by standard protocols, with the resultant, pure recombinant propagated and stored, such as at 4° C. and −80° C. Standard protocols are described, for example, in O'Reilly, Miller and Luckow, *Baculovirus Expression Vectors, A Laboratory Manual*.

EXAMPLE 2

The activities of four different insect toxins towards two different insects and towards mice were determined (since one prefers to use insect toxins that have little or no effect on mammals). These were purified by established methods from the respective crude venoms. Their toxicity towards mice and larvae of blow fly and lepidoptera was determined according to the method of Reed and Muench (1938).

Table 2 shows the activity of the toxins towards insects and mice in terms of fifty percent end points (paralytic or lethal doses $PU_{50}$, $LD_{50}$ respectively). The $PU_{50}$ values of the toxins to blow fly larvae were in accordance with previously published results (Zlotkin et al., *Biochim*, 53, 1075–1078 (1971); and Eitan et al., *Biochem*., 29, 5941–5947 (1990)). The toxicity of those toxins towards the lepidopterous larvae of *Heliothis virescens* is comparable to their toxicity to larvae of *Spodoptera littoralis*. LqhαIT showed higher toxicity towards mice (Swiss Webster), but the other toxins showed no toxicity to mammals (3 μg/g b.w injected subcutaneously had no effect, in contrast to the $LD_{50}$ of a mammalian toxin $AaH_{II}$—0.018 μg/20 g b.w (DeLima et al., 1986). The toxins LqhIV and LqhVI are of considerable interest since LqhIV is the most potent lepidopterous toxin isolated from scorpion venom to date while the toxin LqhVI has weak mammal toxicity.

TABLE 2

| Toxins | $PU_{50}$ to *Sarcophaga falculata* larvae (μg/100 mg b.w.)[a] | $PU_{50}$ to *Heliothis virescens* larvae (μg/100 mg b.w.)[b] | $LD_{50}$ to Swiss Webster mice (μg/ 20 g b.w.)[c] |
|---|---|---|---|
| AaIT | 0.0025 | 2.5 | >60 |
| LqhIT$_3$ | 0.050 | 2.5 | >60 |
| LqhIT$_2$ | 0.025 | 2.5 | >60 |
| LqhαIT | 0.0025 | 2.5 | 8.0 |
| LqhIV | 0.1 | 0.5 | 12 |
| LqhVI | 0.006 | 3.0 | >60 |

[a]Three replicates of 25–40 blow fly larvae each were injected with each one of the toxins and the $PU_{50}$ were determined. The $PU_{50}$ of the excitatory toxins AaIT, LqhVI, and LqhIT$_3$ was determined as a contraction paralysis immediately after injection. The $PU_{50}$ of the depressant toxin LqhIT$_2$ was determined as a flaccid paralysis 5 minutes after injection. The $PU_{50}$ of the α insect toxins LqhαIT and LqhIV was determined as a delayed and sustained contraction paralysis 5 minutes after injection.
[b]Three replicates of 25–40 lepidopterous larvae each were injected with each one of the toxins and the $PU_{50}$ was determined as inability to move or turn when inverted on its back 24 hours after injection.
[c]Two replicates of eight mice were injected subcutaneously and the $LD_{50}$ to mice was determined 24 hours after injection.

EXAMPLE 3

Combinations of toxins were injected simultaneously, and toxicity was measured as summarized in Table 3. The toxin combinations included amounts corresponding to 1 $PU_{50}$ unit of each toxin and their dilutions. Pairs of toxins that do not compete with each other on the same binding site and differ in their pharmacology were synergistic. As shown in Table 3, the degree of cooperatively is not only dependent on the toxin combinations but also on the test animal.

TABLE 3

| Toxin | PU$_{50}$ to *Sarcophaga falculata* larvae (μg/100 mg b.w.)[a] | | PU$_{50}$ to *Heliothis virescens* larvae (μg/100 mg b.w.)[b] | | LD$_{50}$ to Swiss Webster mice (μg/20 g b.w.)[c] | |
|---|---|---|---|---|---|---|
| | Dose | Change in Potency* | Dose | Change in Potency* | Dose | Change in Potency* |
| AaIT + LqhIT$_2

B in 70 min, the flow rate was 0.6 ml/min. Absorbance was monitored at 214nm and peaks collected accordingly LqhVI was purified from CM-III as follows: buffer A was 5% ACN with 0.1% HFBA and buffer B was 95% ACN with 0.1% HFBA. The column was equilibrated in buffer A and eluted with a linear gradient of 0–90% B in 105 min, the flow rate was 0.6 ml/min. Absorbance was monitored at 214 nm and peaks collected accordingly. The eluted fractions were collected and tested for activity (Table 2) and purity.

Purity of Toxins

The homogeneity and purity of LqhIV and LqhVI was tested by Free Solution Capillary Electrophoresis (Applied Biosystems Model 270A). The capillary was equilibrated with 20 mM Sodium citrate pH=2.9 and the samples (0.02 mg/ml protein) were loaded using vacuum for two seconds. The running buffer was 20 mM sodium citrate pH=2.9, the electric force was 20KV.

Sequence Determination

20 μg of each toxin were reduced and carboxymethylated using established method (Fernandez et al., "Techniques in Protein Chemistry," Vol. 5 page 215). The N-terminal sequence was determined using HP sequence analyzer by automated Edman degradation. Reduced and carboxymethylated LqhIV was digested using Endoproteinase Asp-N and peptides were generated. Separation of the digested peptides was done on microbore HPLC (Ultrafast Microprotein analyzer- Michrom BioResources Inc) using polymeric column. Buffer A was 5% ACN with 0.1% TFA and buffer B was 95% ACN with 0.1% TFA. The column was equilibrated in buffer A and eluted with a linear gradient of 0–50% B in 50 min, the flow rate was 0.05 ml/min. Absorbance was monitored at 214 nm and peaks collected accordingly. Peptide P2 was sequenced in order to determine the full amino acid sequence of the toxin.

EXAMPLE 6

Binding Protocol

Preparation of Insect Neuronal Membranes

All dissections and preparations of insect neuronal tissues are performed in a cold buffer of the following composition: 0.25 M mannitol, 10 mM EDTA pH=7.4, 5 mM HEPES (adjusted to pH 7.4 with Tris), 50 μg/ml phenylmethylsulfonyl fluoride, 1 μM pepstatin A, 1 mM iodoacetamide and 1 mM 1,10-phenantroline. Insect nervous tissues are dissected and homogenized in ice cold buffer, the debris is removed by centrifugation at 1,000 g for 10 min. The supernatant is centrifuged at 27,000 g for 45 min and the membranes are collected ($P_2$). The $P_2$ is suspended in the buffer and adjusted to 10% Ficoll (in the buffer) and centrifuged at 10,000 g for 75 min. The resulting floating pellicle representing the enriched synaptosomal fraction is collected. Following treatment by hypotonic medium (5 nM Tris-HCl pH=7.4, 1 mM EDTA, 50 μg/ml phenylmethylsulfonyl fluoride, 1μM pepstatin A, 1 mM iodoacetamide and 1 mM 1,10-phenantroline) membrane vesicles are formed. The membrane vesicles are collected in a small volume of dissection buffer after centrifugation 27,000 g for 45 min and stored at –80° C. until use.

Radioiodination of Toxins

The toxins are iodinated by iodogen (Pierce Chemical Co., Rockville, Md.) using 0.5 mCi of carrier-free Na $^{125}$I (~0.3 nmol) (Amersham) and 5 mg (~0.7 nmol) of toxin. The monoiodotoxin is purified on HPLC using a Beckman Ultrapore C3 RPSC column (4.6×75 mm) fractions are eluted at gradient of 10–80% solvent B (solvent A=0.1% TFA, solvent B=50% ACN, 50% 2-propanol and 0.1% TFA) at flow rate of 0.5 ml/min. The monoiodotoxin is eluted as the first peak of radioactive protein (about 30% solvent B) following the peak of the native toxins (about 28% solvent B). The concentration of the radiolabeled toxin is estimated according to the specific radioactivity of $^{125}$I and correspond to 2424 dpm/fmol monoiodotoxin.

Binding Assays

Competitive binding assays are performed at equilibrium conditions using increasing concentrations of an unlabeled toxin in the presence of a constant concentration of a labeled toxin. Analysis of all binding assays is performed using the iterative computer program LIGAND (P. J. Munson and D. Rodbard, modified by G. A. McPherson 1985). Insect membrane vesicles are suspended in binding medium containing 0.13 M choline chloride, 1 mM EDTA pH=7.4, 20 mM HEPES/Tris pH=7.4 and 5 mg/ml BSA. Following 1 hour incubation with the toxins, the reaction mixture is diluted with 2 ml ice-cold wash buffer (150 mM choline chloride, 5 mM HEPES/Tris pH=7.4, 1 mM EDTA pH=7.4 and 5 mg/ml BSA) and filtered over GF/F filters (Whatman, U. K.) under vacuum, followed by two more washes of the filters with 2 ml of wash buffer each time. Non-specific toxin binding is determined in the presence of 1 μM unlabeled toxin.

EXAMPLE 7

Construction of the Synthetic Gene (FIG. 1. SEQ ID NO:1)

The protein sequence of a toxin was converted into a nucleotide sequence using the preferred codon usage of a baculovirus. The toxin gene along with the nucleotide sequence of a leader sequence (bombyxin, native leader or other) and the appropriate restriction enzyme sites were used to design and synthesize 5 complementary pairs of oligonucleotides. The oligonucleotides were phosphorilated, annealed, ligated and amplified by PCR using the outside oligonucleotides as primers. The PCR product is blunt end ligated into a PCRscript plasmid and the correct sequence was confirmed by sequencing. A BamHI restriction fragment was rescued from this plasmid cloned into a baculovirus transfer vector under a baculovirus promoter (P10, polyhedrin, Basic, IE1 etc.). A plasmid containing the correct sequence of the gene and leader sequence was confirmed by sequencing. Using the resulting transfer vector and the standard procedures a recombinant virus expressing the toxin was constructed.

Construction of a Virus Expressing AaIT and LqhIV

The leader sequence of bombyxin and the gene coding for the toxin LqhIV were designed and synthesized as described above. The correct sequence was confirmed and the gene was cloned into a double expression transfer vector already containing the AaIT gene. The transfer vector pAcUW51P2 is a polyhedrin positive vector with two cloning sites, a BglII site and the LqhIV gene with the bombyxin leader were cloned into the BamHI site. Sf21 cells were cotransfected with the resulting transfer vector and infectious virus particles using the lipofectin procedure. Recombinant viruses were selected as a polyhedrin positive phenotype in a standard plaque assay. Sf21 cells were inoculated with the recombinant virus AcAaLq according to standard procedures. Protein extracts from virus infected cells were separated on 15% SDS-PAGE gels and then electroeluted to nitrocellulose membranes. The membranes were probed with AaIT and LqhIV antibodies, bound antibodies were detected using rabbit IgG HRP conjugates.

In conclusion, genetically engineered, insecticidal microbes are produced in accordance with the invention and then used to control a variety of pests. In doing so, one may use a single recombinant virus expressing a plurality of neurotoxins. The combination of toxins are determined by selecting toxins that act at the same cellular channels (typically sodium channels) but at non-overlapping sites.

Alternatively, one may use two (or more) recombinant insecticidal microbes where each expresses a different toxin. Again, the several expressed toxins are selected as already described. These combinations of expressed toxins accelerate the rate of kill of pests by the virus or viruses beyond simply an "additive" function. For example, the lethality of toxins AaIT and LqhαIT in both blowfly larvae and in Heliothis larvae was increased 5–10 fold when used in combination. Further, the combinations of toxins can be used to enhance selectivity within insect groups.

Conventional application means of the recombinant microbes (spraying, atomizing, dusting, scattering, or pouring) may be used from formulations such as powders, dusts, granulates, as well as encapsulations such as in polymer substances. Compositions will typically include inert carriers such as clay, lactose, defatted soy bean powder, and the like to assist in applications, in order to apply the recombinant microbes expressing synergistic combinations of insecticidal toxins.

It is to be understood that while the invention has been described above in conjunction with preferred specific embodiments, the description and examples are intended to illustrate and not limit the scope of the invention, which is defined by the scope of the appended claims.

It is claimed:

1. A substantially pure insect toxin, useful in insect control, expressed from SEQ. ID NO: 1 or having the amino acid sequence SEQ. ID NO:2.

2. A method of using a recombinant baculovirus, comprising:

providing a recombinant baculovirus which, in insect cells of selected insects infected therewith, expresses a plurality of toxins, each toxin binding to the same membrane ion channel at a non-overlapping binding site with respect to the other toxin or toxins and each toxin having an insecticidal potency for the insect cells of the selected insects, the plurality oftoxins together having a greater insecticidal potency for insect cells of the selected insects than would be achieved from an additive effect of each toxin alone; and, infecting insects with said recombinant baculovirus.

3. The method as in claim 2 wherein the baculovirus is a nuclear polyhedrosis virus.

4. The method as in claim 2 wherein the baculovirus is *Autographa califonica*.

5. The method as in claim 2 wherein at least one toxin is a component of scorpion, wasp, snail, mite, or spider venom.

6. A method of using an insecticidal composition, comprising:

providing a first recombinant baculovirus expressing a first toxin, and a second recombinant baculovirus expressing a second toxin, wherein both the first and second toxins bind to the same ion channel but at non-overlapping sites, the first toxin and the second toxin together having an insecticidal potency for selectable insect species greater than would be achieved from an additive effect of each toxin alone; and, infecting insects with said first and second recombinant baculovirus.

7. The method as in claim 6 wherein the first and second recombinant baculoviruses are from *Autographa califomica, Anagrapha falcifera, Anticarsia gemmatalis, Buzura suppressuria, Cydia pomonella, Helicoverpa zea, Heliothis arrigera, Mariestia brassicae, Plutella xylostella, Spodoptera exigua, Spodoptera littoralis*, or *Spodoptera litura*.

8. The method as in claim 7 wherein the first and second toxins are combinations of AaIT, LqhIT$_2$, LqhαIT, and LqhIT$_3$ neurotoxins.

9. The method as in claim 7 wherein the selectable insect species is *Heliothis virescens* or blow fly.

* * * * *